United States Patent
Rito Palomares et al.

(10) Patent No.: US 8,178,321 B2
(45) Date of Patent: May 15, 2012

(54) **RECOVERY AND PURIFICATION OF B-PHYCOERYTHRIN PRODUCED BY *PORPHYRIDIUM CRUENTUM* USING TWO-AQUEOUS-PHASE SYSTEMS AND ISOELECTRIC PRECIPITATION**

(75) Inventors: Marco Antonio Rito Palomares, Monterrey (MX); Jorge Alejandro Benavides Lozano, Monterrey (MX); Tanhia Denys Hernandez Mireles, Monterrey (MX)

(73) Assignee: Instituto Tecnologico y de Estudios Superiores de Monterrey, Monterrey (ME)

( * ) Notice: Subject to any disclaimer, the term of this patent is extended or adjusted under 35 U.S.C. 154(b) by 536 days.

(21) Appl. No.: 12/440,458

(22) PCT Filed: Aug. 16, 2007

(86) PCT No.: PCT/MX2007/000095
§ 371 (c)(1),
(2), (4) Date: Mar. 6, 2009

(87) PCT Pub. No.: WO2008/030076
PCT Pub. Date: Mar. 13, 2008

(65) Prior Publication Data
US 2010/0178674 A1     Jul. 15, 2010

(30) Foreign Application Priority Data
Sep. 6, 2006   (MX) .................. NL/a/2006/000062

(51) Int. Cl.
*C21P 21/00*     (2006.01)
(52) U.S. Cl. ..................................... 435/71.1
(58) Field of Classification Search .............. None
See application file for complete search history.

(56) References Cited

OTHER PUBLICATIONS

PCT/MX07/000095 Search Report, Dec. 13, 2007, Instituto Technologico y de Estudios Superiores de Monterrey.
Hernandez-Mireles, T., et al., "Improved recovery of B-phycoerythrin produced by the red microalga *Porphyridium cruentum*," Journal of Chemical Technology and Biotechnology, vol. 81:989-996, Jun. 2006.
Hernandez-Mireles, T., et al., "Proceso para la purificación del colorante proteico B-ficoeritrina producido por *Porphyridium cruentum*," "Process to purify the colored protein B-phycoerythrin produced by *Porphyridium cruentum*," Revista Mexicana de Ingenieria Quimica, vol. 5, No. 2, pp. 131-143, 2006.
Benavides, J., et al., "Bioprocess intensification: a potential aqueous two-phase process for the primary recovery of B-phycoerythrin from *Porphyridium cruentum*," Journal of Chromatography B, vol. 807, No. 1, pp. 33-38, 2004.
Benavides, J., et al., "Potential aqueous two-phase processes for the primary recovery of colored protein from microbial origin," Engineering in Life Sciences, vol. 5, No. 3, pp. 259-266, 2005.
Hernandez-Mireles, T., et al., "New aqueous two-phase systems based on poly(ethylene oxide sulfide) (PEOS) and potassium phosphate for the potential recovery of proteins," Journal of Chemical Technology and Biotechnology, vol. 81, No. 6, pp. 997-1002, Jun. 2006.

Primary Examiner — Tekchand Saidha
Assistant Examiner — Mohammad Younus Meah
(74) Attorney, Agent, or Firm — Baker & McKenzie LLP

(57) ABSTRACT

This invention focuses on a novel process in which *Porphyridium cruentum* biomass first undergoes a stage of cellular disruption and subsequently stages of recovery and purification in order to achieve the purified B-phycoerythin (BFE) protein dye, using isoelectric precipitation and two-aqueous-phase systems. The steps of recovery and purification include isoelectric precipitation followed by a step of liquid/liquid extraction by means of two-aqueous-phase systems that use polyethylene glycol (PEG) and phosphate salts. The BFE protein dye obtained in the two-aqueous-phase extraction step undergoes an ultrafiltration step in order to remove the polymer (PEG) and to obtain a dye with a purity greater than 4.0 defined as the relationship between the absorbencies at 545 and 280 nm (BFE purity=Abs 545 nm/Abs 280 nm).

24 Claims, 3 Drawing Sheets

RECOVERY AND PURIFICATION OF B-PHYCOERYTHRIN PRODUCED BY *PORPHYRIDIUM CRUENTUM* USING TWO-AQUEOUS-PHASE SYSTEMS AND ISOELECTRIC PRECIPITATION

CROSS-REFERENCE TO RELATED APPLICATIONS

This application is a 35 U.S.C. Section 371 of PCT/MX2007/000095, filed Aug. 16, 2007, which claims priority to Mexico Application No. NL/a/2006/000062, filed Sep. 6, 2006, which are incorporated herein by reference in their entirety.

SUBJECT OF THE INVENTION

The invention relates to the development of a process for recovery and purification of B-phycoerythrin (BFE) produced by *Porphyridium cruentum* (ATCC No. 50161), having as principal steps of isoelectric precipitation and two-aqueous-phase systems with polyethylene glycol (PEG) and potassium phosphate.

PRIOR ART

The use of artificial colorants (particularly in the food and cosmetics industry) has decreased considerably as a result of adverse health effects which some colorants have been shown to have. Among such effects are mental changes (particularly in children), development of allergic reactions, and cancer. For this reason, and consumer pressure on companies which use artificial colorants, the use of colorants of natural origin has become popular. Also, natural colorants have turned out to be quite versatile, with applications not only in food and cosmetics but also in research applications (particularly in the area of molecular biology).

The phycobiliproteins are proteinaceous colorants which are found in nature (in cyanobacteria, eukaryotic monocellular biflagellates, and rhodophyta, members of the class Rhodophyceae). These compounds are considered as accessory pigments which facilitate the process of photosynthesis in these organisms. They are located in the chloroplasts (thylakoid membrane). The phycobiliproteins have linear tetrapyrrole prosthetic groups (bilins) which are covalently linked to specific cysteine groups of proteins (Bennejo et al., 2002; Berns and MacColl, 1989; Ritter et al., 1999). These complexes absorb light in a wide range of wavelengths in the visible spectrum, and thus encompass a wide range of colors. B-phycoerythrin (BFE) is an intense red colored phycobiliprotein, with molecular weight 245 kDa, formed from three subunits ($\alpha$, $\beta$, and $\gamma$, in a molar ratio of 6:6:1), of molecular weights 18,000, 18,000 and 29,000 g/mol, respectively (Benavides and Rito-Palomares, 2004). The isoelectric point of BFE has been reported to be in the range 4.2-4.4 (Koller et al., 1977), which enables the use of gel electrophoresis to separate this protein. The marine microalga *Porphyridium cruentum* (ATCC No. 50161) has demonstrated high potential for production of BFE. This proteinaceous dye has been shown to have applications in the food, cosmetic, and detergent industry as a natural colorant. It is also widely used as a fluorescent colorant in molecular biology (Bermejo et al, 2002). The commercial price of BFE of high purity (defined by the absorption ratio Abs 545 mm/280 mm>4) has been reported as USD 50/g (Martek Corp., 2005; Haugland, 1996). *Porphyridium cruentum* also produces other colorants which are phycobiliproteins (e.g. allophycocyanin (AFC) and R-phycocyanin (RFC). The commercial prices commanded by these colorants are not as high as for BFE, and thus development of a method of recovery and purification of these colorants is not as attractive. In contrast, the high commercial price of BFE has justified intense prior efforts at development of efficient processes for the recovery and purification of BFE (Bermejo et al., 2002 and 2003; Univ. Granada, Spanish patent documents ES 2197820 A1 and ES 2197820 B1).

Despite the substantial versatility of natural colorants, their use has been burdened to some degree by the complexity of the processes for recovery and purification needed to produce them. Also, process costs are high, as a result of the large number of operations involved. The techniques are not well scalable, and thus their use on an industrial scale gives rise to elevated operating and maintenance costs, which has rendered materials of this nature less attractive to recover and produce.

Protocols for recovery and production of B-phycoerythrin produced by various producers have been reported, for a wide range of applications. In Chinese Patent CN 1587275 A a method of recovery and purification of B-phycoerythrin was disclosed in which the B-phycoerythrin is produced by microalgae, wherewith the process stages involve leaching with distilled water, stepwise precipitation with ammonium sulfate, and ion exchange chromatography; this results in a recovery of approximately 52%. In Spanish patent documents ES 2197820 A1 and ES 2197821 B1 it is reported that purified BFE from *Porphyridium cruentum* was produced via cellular disruption by osmotic shock, followed by a stage of chromatographic separation in an "expanded bed" with an ionic support (average yield is 80%), and finally a conventional ionic chromatographic stage, yielding a highly purified product (Abs 545 mm/280 mm>4). In patents TW 222463 B 1, TW 222999 B1, TW 223000 B1, TW 224135 B1 and patent applications TW 200408706 A, TW 200408707 A, TW 200408704 A, TW 200408705 A, JP 2004166704 A, and US 20040137583 A1 a process of production and recovery of phycoerythrin is reported wherein the phycoerythrin is produced by algae, with the microorganism being cultured with the use of two tanks in series, and involving generation of a solution of chromoproteins, subsequently recovering the phycoerythrin present in the solution by sedimentation, and purifying it using costly techniques such as filtration gel chromatography and ultrafiltration, whereby BEF of a "purity" Abs 545 mm/280 mm>4 is obtained. Japanese Patent Application JP 2003231821 A reports a method of recovery of colorants produced by algae which method involves drying of the biomass, re-suspension in a solution of ammonium sulfate or another particular buffer, and then a stage of selective separation. In Taiwanese Patent TW 270146, phycoerythrin produced by *Bangia atroprpurea* and *Porphyra angusta* is recovered by a process which involves collection of gametophytes from mature algae, culturing of these gametophytes in a special medium to produce spores, culturing of the spores under controlled conditions of temperature and light, culturing of the filamentous bodies formed by the spores, collection, drying, and re-suspension of the bodies in a phosphate solution with extraction of the colorants of interest and other contaminants, adding salts to precipitate-out impurities, and finally the use of gel chromatography to purify the phycoerythrin. Although this method produces highly purified phycoerythrin, the method is relatively complex, and its application on an industrial scale is limited, as is application of the processes disclosed in Japanese Patent JP 2648088 B2 and U.S. Pat. No. 5,358,858 A.

As seen, at present there are few reported methods of recovery and purification of intracellular proteinaceous colorants produced by algae. Moreover, in most cases the process as developed is complex because it employs a number of chromatographic stages which are needed to obtain the protein of interest in the necessary purity (Bermejo et al., 2002 and 2003). The need for a substantial number of steps which is a characteristic of the conventional methods results in losses of products and relatively low yields, as well as high process costs (Ranjitha and Kaushik, 2005). Consequently, the potential scalability of such methods is viewed negatively from the economic standpoint.

The object of the present invention was to devise a process for recovery and purification of BFE using isoelectric precipitation and two-aqueous-phase systems (comprising a PEG and a salt), which techniques are easily scalable to an industrial scale and moreover give a BFE of high purity. This corresponds to the publication of Hernández-Mireles and Rito-Palomares (2006) (authors of the present patent application), which describes a method of recovery and purification of BFE using isoelectric precipitation and two-aqueous-phase systems (comprising a PEG and a salt). The process proposed herein is derived from that study.

Isoelectric precipitation is a technique which is widely used for recovery and purification of proteins; it is based on the fact that the isoelectric point is a pH value at which the surface charge of a given molecule (protein) is equal to zero. The solubility of a protein which is at its isoelectric point is minimal because there is no surface electric charge, and thus the forces of repulsion between the molecules disappear, allowing formation of aggregates which readily precipitate. This phenomenon is referred to as "isoelectric precipitation". This technique for recovery and purification of proteins is widely used (Onsaard et al., 2006; Zhang et al., 2004) because it is economical and is easy to implement on any scale. Suitable developed processes which include isoelectric precipitation, among other steps, for recovery and purification of BFE can achieve a high "purity," in particular, analytical purity (Abs 545 mm/280 mm>4) (Bermejo et al., 2003). However, these processes for recovery and purification employ a large number of steps, which tend to include chromatographic steps. The high number of unit operations generates unnecessarily high losses of the product of interest. While chromatography is a technique which can be adapted to use on an industrial scale, the scale-up entails high costs of investment, operation, and maintenance. Economic studies report that methods employing two-aqueous-phase systems (TAPSs) can be realized at relatively low investment and operation costs compared to chromatography (Aguilar et al., 2006). For this reason, and by reason of other intrinsic advantages of two-aqueous-phase systems, it was decided to develop a process which incorporates the techniques of isoelectric precipitation and two-aqueous-phase systems, for recovery and purification of BFE.

Due to the fact that TAPS is primarily a liquid-liquid technique for recovery and purification, it has been demonstrated to be efficient for separation of biological compounds (proteinaceous and non-proteinaceous) (Rito-Palomares, 2004 and 2002; Shinomiya et al., 2003; Kepka et al., 2003; Cunha et al., 2003; Marcos et al., 2002; Reh et al., 2002). TAPSs enable intensification and integration of the processes of recovery, because they can process large quantities of suspended solids (including cellular residues), such that unnecessary operations can be eliminated (e.g. centrifugation and precipitation); thus they combine two or more steps into one. Also, TAPSs are relatively economical and are readily scalable, making them ideal candidates for inclusion in a process on an industrial scale.

There are known "polymer-polymer" TAPSs which employ different polymers (e.g. PEG and dextran; or PEG and polyvinyl alcohol). However, the use of such systems is limited to a certain extent by the high costs of some of the polymers used. Numerous polymers are known to form systems of two aqueous phases when combined with certain salts, forming a TAPS comprised of a polymer and a salt (e.g. PEG and potassium phosphate, or PEG and sodium sulfate) (Huddleston et al., 1991; Albertsson et al., 1990). The tendency of a compound to migrate to a particular phase in a system depends on various factors, including: the molecular weight of the compound, its net electrochemical charge, its isoelectric point, and its content of hydrophobic amino acid groups. The partition behavior is not influenced solely by its own characteristics but also by the parameters of the TAPS itself, which play a large role during the partition of the protein of interest between the phases. These TAPS parameters include (inter alia): the type of system, the molecular weight and concentration of the polymer used in the system, the nature and concentration of the salts used, differences in the concentration of components in each of the phases, the pH of the system, and the temperature (Sarubbo et al., 2000). Due to the low cost and the short duration of the separation process, one of the well described and prevalently used TAPSs is the system PEG/potassium phosphate.

The process proposed in the present document allows recovery and purification of B-phycoerythrin produced by *Porphyridium cruentum*. This process comprises a step of isoelectric precipitation, and two-aqueous-phase systems, and achieves a "purity" of the B-phycoerythrin of greater than 4 (Abs 545 mm/280 mm>4), thereby allowing the resulting product to be used in applications related to molecular biology.

DETAILED DESCRIPTION OF THE INVENTION

Figure 1:
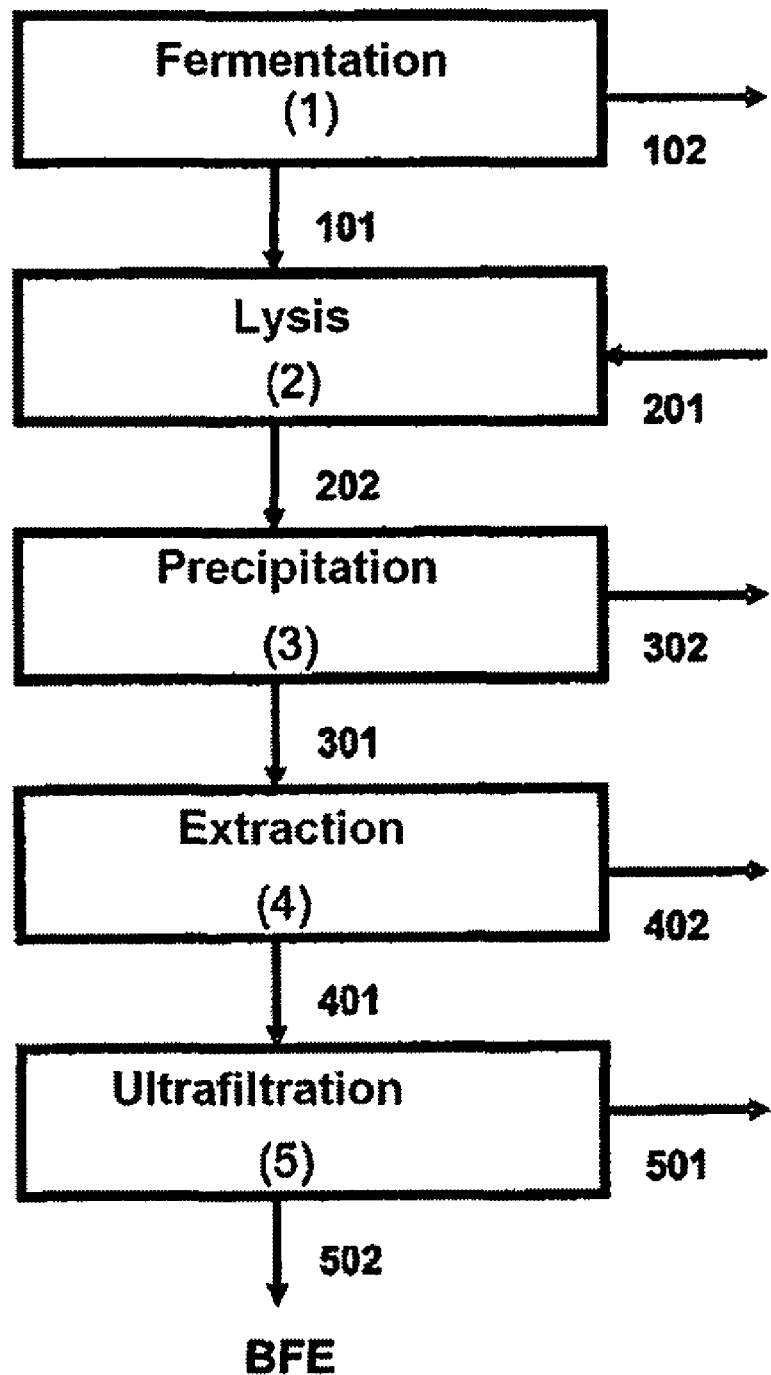
FIG. 1 is a simplified flow diagram of the proposed process for recovery and purification of BFE produced by *Porphyridium cruentum*.

The present invention relates principally to a novel method of recovering and purifying BFE produced by the microalga *Porphyridium cruentum* (ATCC No. 50161), using two principal process steps as follows—a step comprising a two-aqueous-phase separation system comprising a polymer-containing aqueous phase and a salt-containing aqueous phase and an isoelectric precipitation step. The invention contemplates three principal steps subsequent to the culturing of the microalga. The protocols for the culturing of microalgae are well documented and standardized (Cohen et al., 1991; Cohen and Arad, 1989); the application of these techniques on the laboratory and industrial scale is facilitated by the cited references. The composition of the culture medium used for culturing the *Porphyridium cruentum* is presented in Table 1.

The culturing of the alga is carried out in a batchwise or continuous mode, at 18-25° C., under conditions of natural or controlled light (5-300 microeinstein per sq m per sec). The walls of the bioreactor should be of a transparent material (e.g. glass or plastic) which allows free passage of the light.

During the culturing, the reactor should be agitated and supplied with air in the form of 2-4 cm³ per second per cu dm of the cultivar mixture. The addition of carbon dioxide is optional, but it is recommended that carbon dioxide be added to the air flow to the bioreactor in a concentration of 1-5 vol %, with the aim of accelerating the growth of the algae and increasing the cellular density. The cells continue in a growth mode for 15 days if the culture is supplemented with CO2, whereas without addition of CO2 the culturing process may require 30 days.

TABLE 1

Composition of the culture medium for *Porphyridium cruentum*

| Compound | Chemical formula | Amount per liter |
|---|---|---|
| Sodium chloride | $NaCl$ | 24.53 g |
| Magnesium chloride | $MgCl_2$ | 5.20 g |
| Sodium sulfate | $NaSO_4$ | 4.09 g |
| Calcium chloride | $CaCl_2$ | 1.16 g |
| Potassium chloride | $KCl$ | 0.70 g |
| Sodium bicarbonate | $NaHCO_3$ | 0.20 g |
| Sodium nitrate | $NaNO_3$ | 0.17 g |
| Potassium bromide | $KBr$ | 0.10 g |
| Boric acid | $H_3BO_3$ | 30.00 g |
| Monobasic sodium phosphate | $NaH_2PO_4$ | 14 mg |
| Disodium EDTA | $NaC_{10}H_{14}N_2O_8$ | 10 mg |
| Ferrous citrate | $Fe_3(C_6H_5O_7)_2$ | 5 mg |
| Sodium molybdate | $Na_2MoO_4$ | 0.24 mg |
| Manganous chloride | $MnCl_2$ | 0.20 mg |
| Zinc chloride | $ZnCl_2$ | 0.14 mg |
| Cupric sulfate | $CuSO_4$ | 0.03 mg |
| Cobaltous chloride | $CoCl_2$ | 0.01 mg |
| Thiamine | $C_{12}H_{17}N_4OS$ | 35 ug |
| Biotin | $C_{10}H_{16}N_2O_3S$ | 5 ug |

Separation of the biomass. In the first step, the cells of the algae (also known as the "biomass") are recovered by traditional steps of solid-liquid separation, such as centrifugation or sedimentation. Centrifugation is preferred because it allows recovery of a greater fraction of the suspended biomass and it is significantly faster than sedimentation. The centrifugation conditions selected may be intensity 100-10,000 G and duration 2-10 minutes. With these conditions it is possible to recover essentially all of the biomass suspended in the culture mixture. The quantity of biomass obtained depends strongly on the culture conditions chosen (culture medium, light cycle, natural or controlled light, supplementation with $CO_2$, and duration of culture). This quantity may typically be in the range 5-40 g wet biomass per liter of culture mixture.

Cellular disruption. Subsequently, considering that BFE is an intracellular product, it is necessary to liberate the colorant by a cellular disruption technique. The available techniques for cellular disruption are mechanical (e.g. maceration and ultrasound exposure) and non-mechanical (e.g. chemical and enzymatic lysis). A mechanical technique is preferred for reasons of efficiency and the fact that external agents (chemical and/or enzymatic) do not need to be added. Accordingly, after the cells are recovered a mechanical method of disruption of the cells is carried out (e.g. manual maceration and/or ultrasound exposure). Ultrasound exposure is accomplished as follows: A specified weight of the wet biomass of *Porphyridium cruentum* (ATCC No. 50161) is placed in a glass vessel, and 2-10 cc double distilled water is added per gram of wet biomass. The mixture is agitated manually by inverting the vessel until the cells are in suspension. The container with the suspended cells is exposed to ultrasound for 2-20 minutes for each gram of wet biomass added to the vessel. An alternative technique for cellular disruption of *Porphyridium cruentum* (ATCC No. 50161) is manual maceration, which is accomplished as follows: A specified weight of wet biomass is added to a mortar, and 2-10 cc double distilled water is added per gram of wet biomass present. The mixture is macerated manually for 2-20 minutes for each gram of biomass added. Even though it is possible to use either method to disrupt the cells of *Porphyridium cruentum* (ATCC No. 50161), the ultrasound technique is more efficient for liberating BFE; it allows liberation of a greater quantity of BFE per gram of wet biomass processed. Moreover, ultrasound exposure liberates proportionally less allophycocyanin (AFC) and R-phycocyanin (RFC) in relation to the BFE. The purity of BFE with respect to other proteins (defined as the ratio of the absorbencies at 545 and 280 nm) in the crude extract obtained by ultrasound exposure and/or maceration is generally in the range 0.6-0.8 (abs 545 nm/280 nm=0.6-0.8). The rupturing of the cellular membrane by the disruption technique used (ultrasound exposure or maceration) can be verified with the use of a standard optical microscope (e.g. Carl Zeiss standard model 25). The term "crude extract of BFE" is used to refer to the extract obtained as a result of the disruption of the cells of *Porphyridium cruentum* (ATCC No. 50161); it includes also the cellular fragments generated. The ultrasound technique of cellular disruption is principally employed in laboratory or pilot scale processes; for processing on an industrial scale, other mechanical methods of disruption such as crushing in a ball mill or French press may be used instead, without compromising the quantity or purity of BFE liberated.

Isoelectric precipitation. In the second step of the process, it is proposed to initially purify the crude BFE extract coming from the cellular disruption step with the use of isoelectric precipitation. Isoelectric precipitation is applied to the crude BFE extract obtained from the cellular disruption of *Porphyridium cruentum* (ATCC No. 50161), with adjustment of the pH of the extract to 4-5. This pH adjustment may be achieved with the use of a large variety of acids or bases (inorganic or organic) for decreasing or (respectively) increasing the pH of the extract. In particular hydrochloric acid (HCl), sulfuric acid ($H_2SO_4$), phosphoric acid ($H_3PO_4$), and acetic acid ($C_2H_4O_2$) are acids which are widely used acids which may be employed for adjusting the pH during the isoelectric precipitation of the BFE. Preferably, HCl is used, in a concentration the range 0.1-10 N. Among the widely used bases which may be employed for adjusting the pH during the isoelectric precipitation one may use, in particular, sodium hydroxide (NaOH) or potassium hydroxide (KOH), in a concentration in the range 0.1-10 N. Preferably the process is carried out at a low temperature (5-15° C.) and with the suspension being protected from excessive exposure to light for an extended period of time (a light intensity>20 microeinstein per sq m per second should not be allowed for more than 30 minutes), in order to avoid degradation of the product of interest. It is possible to protect the suspension from light by carrying out the precipitation in an amber colored vessel or by protecting the vessel containing the suspension with aluminum foil or other material which does not permit passage of light.

Recovery of the precipitate by eliminating the supernatant or by other means. The precipitate is recovered by centrifugation (100-2000 G, 10-20 min) and re-suspension using phosphate buffer (20 mM, pH 7.0). The solution obtained as a result of this process is referred to as the "re-suspended BFE extract". The protein of interest is obtained in maximum purity at a pH of 3.5-4.5 (close to the isoelectric point for BFE reported by Koller et al., 1977). At this pH the "purity" of the re-suspended extract is in the range 1.6-2.0 (i.e. Abs 545 nm/280 nm=1.6-2.0). This represents an increase by a factor of 2.6 in the "purity" of the crude extract leaving the cellular disruption step. In the isoelectric precipitation step, approximately 70-80% of the BFE present in the crude extract is recovered in the precipitate; the remainder stays in the supernatant. The precipitate from the isoelectric precipitation is rich in BFE, cellular remnants, and other proteins having an isoelectric point similar to BFE. This precipitate is recovered, re-suspended, and sent to the two-aqueous-phase system.

Adding to the two-aqueous-phase system. Two-aqueous-phase systems are conveniently prepared using a fixed solid base. To form a two-phase system containing polyethylene glycol (PEG) and potassium phosphate, suitable amounts of PEG and potassium phosphate are mixed with the re-suspended extract of BFE (obtained by isoelectric precipitation of the crude extract). In prior studies (Benavides and Rito-Palomares, 2004; Hernández-Mireles and Rito-Palomares, 2006) the system parameters under which distribution of the BFE into the upper phase is favored were determined (namely the conditions for optimum recovery of BFE in the polymeric phase of the system). These conditions are: molecular weight of the polymer (MW PEG) in the range 600-1500 g/gmol; length of the "cut line" (LLC) (which is a function of the difference between the concentration of the PEG and of the salt in each of the phases of the system) in the range 30-50 wt. %; volume ratio ($V_R$) (defined as the ratio between volume of the upper phase and the volume of the lower phase, in the system) greater than 2; and pH of the system between 7 and 8.

The systems are formed by mixing PEG in the form of a concentrated solution (50-80 wt. %) and a solution of potassium phosphate (30-40 wt. %). The pH of the potassium phosphate solution is adjusted to 7-8 by addition of orthophosphoric acid or potassium hydroxide, in a concentration in the range 0.1-10 N, as required. Once the PEG solution and potassium phosphate solution are intermixed, re-suspended BFE extract (of concentration in the range 10-40 wt. %, preferably 40 wt. %) from the extract system is added. The total weight of the system is maintained by addition of water.

Agitation of the two-aqueous-phase system. The system is agitated by intermixing the compounds added. The agitation is accomplished by a rotary inversion mixer, 20-120 rpm, duration 5-10 min.

Separation of the phases of the system. One of two methods may be used—sedimentation or centrifugation. Sedimentation is accomplished by holding the system at rest, allowing the phases to separate naturally. The speed of this separation depends on various factors, including the length of the "cut line" (LLC), the molecular weight of the polymer employed, and the geometry of the system. Separation of the phases by sedimentation occurs in 10-30 minutes with system parameters in the ranges mentioned supra (MW PEG 600-1500 g/gmol, LLC 30-50 wt. %, and $V_R$>2). The use of centrifugation will accelerate the formation of the phases of the system (100-5000 G, 2-20 min). This saves appreciable time in the recovery and purification process. In the two-phase aqueous systems, the compounds and cellular residues from the extracts are concentrated in the particular phase to which they have the greater affinity. BFE, being a proteinaceous colorant, has greater affinity for the upper phase in systems formed with PEG and potassium phosphate. The cellular residues tend to concentrate at the interface of the two-aqueous-phase system, which facilitates elimination of these contaminants. Once the two phases of the system are essentially completely separated, the upper, polymer-rich phase, containing the BFE, is recovered. If the container containing the system has a bottom valve, it is possible to first remove the bottom phase of the system (not containing the BFE), and then to recover the polymeric phase (containing the BFE). An alternative is to recover the top phase by pump means.

Removal of the polymer. After the top phase has been recovered, it is possible to remove the polymer by ultrafiltration (which is easy to implement on an industrial scale). The molecular weight of BFE is 245 kDa. In contrast, the molecular weights of the polymers used to generate the system of aqueous phases is in the range 600-1500 g/gmol. Because of the substantial difference between the molecular weight of the protein and that of the polymer, ultrafiltration is an ideal technique for separating the two materials. The separation molecular weight (MWCO) of the ultrafiltration membrane used may be in the range 10-100 kDa, preferably c. 50 kDa.

To summarize, the process of recovery and purification consists of three principal steps: (i) cellular disruption of the *Porphyridium cruentum* (ATCC No. 50161) by ultrasound exposure (or other mechanical technique); (ii) isoelectric precipitation (pH 4-5) of the crude BFE extract; and (iii) two-aqueous-phase systems involving PEG and potassium phosphate. The described process enables one to obtain highly pure BFE (Abs 545 nm/280 nm>4) which can be utilized in molecular biology applications.

Determination of the purity and concentration of the BFE. The total protein concentration of the samples was evaluated using the analytical method of Bradford (1976). The "purity" of the BFE was determined as the ratio between absorbency at 545 nm and 280 nm (Abs 545 nm/280 nm). Bermejo et al. (2002) reported use of the ratio of the absorbencies at 545 and 280 nm as a means of evaluating the purity of BFE, taking account the peak at 545 nm in the absorption spectrum of BFE. Under the circumstances reported, a ratio of these absorbencies of >4.0 corresponds to highly pure BFE (which Sigma Chemicals designates "commercially pure"). The concentration of BFE and the other intracellular proteins RFC and AFC produced by *Porphyridium cruentum* (ATCC No. 50161) can be estimated by exploitation of their absorbencies at 565, 620, and 650 nm, with a system of equations which has been published (Bermejo et al., 2002; Bennet and Bogorad, 1973). The basis of this method is the constant coefficient of extinction which these phycobiliproteins (BFE, RFC, and AFC) exhibit at the wavelengths 565, 620, and 650 nm in an optical density range (OD range) of 0.05-1.0 (Bennet and Bogorad, 1973). To evaluate the absorbencies, one may employ a spectrophotometer with an operating range in the visible and UV range.

Example 1

Proposed Method of Recovery and Purification of BFE Produced by *Porphypridium cruentum*

With reference to FIG. 1, *Porphyridium cruentum* is cultured in a bioreactor (1) under conditions previously reported hereinabove. By centrifugation (1000 G, 5 min) the biomass (101) is separated from the spent culture medium (102). Distilled water in the amount of 4 cc per gram of wet biomass (201) used is added to the biomass, and the microalga is subjected to mechanical cellular disruption (2) by ultrasound exposure (10 min/g of wet biomass used). The pH of the homogenizate resulting from the cellular disruption (comprised of the protein of interest (BFE) and contaminants (including cellular residues)) is adjusted to 4 by addition of 1.0 N HCl to bring about isoelectric precipitation (3), at 10° C. To protect the sample from excessively long exposure to light at excessively high levels (>20 microeinstein per sq m per second) the container is covered with aluminum foil during the isoelectric precipitation. The resulting precipitate (301), comprised of BFE, cellular residues, and other proteins with pI similar to BFE, is recovered, and the supernatant (302), which has a low content of BFE, is discarded. The isoelectric precipitate is re-suspended in phosphate buffer (20 mM, pH 7) and is added to the two-aqueous-phase systems comprising PEG and potassium phosphate (4). After the addition of the precipitate, the system is mixed using a rotary inversion mixer (60 rpm, 10 min), and the phases are separated by means of centrifugation (1000 G, 10 min). The upper phase (401) (containing BFE) is recovered by suction, using a pipette, and after the upper phase has been recovered the lower phase (402) is discarded. The recovered upper phase (401) is subjected to ultrafiltration using a laboratory-scale ultrafiltration cell (5). The recovered upper phase is introduced into the ultrafiltration chamber in which the ultrafiltration membrane has already been installed. The membrane used has pore size suitable for 50 kDa; the propellant is nitrogen gas at pressure 30 psi, which causes separation of the polymer (501) (which passes through the ultrafiltration membrane) from the BFE (502) (which is retained on the membrane). The BFE obtained by this process is of analytical purity (Abs 545 nm/280 nm>4).

Example 2

Cellular Disruption to Liberate the Proteinaceous Colorant

Figure 2:
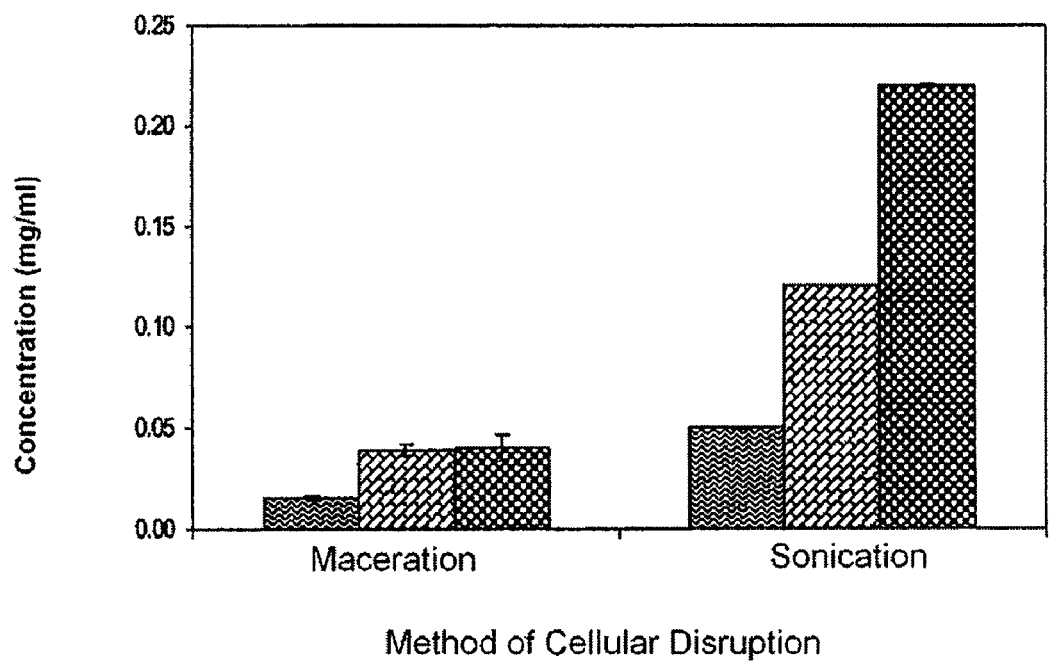
FIG. 2 shows the effects of two different methods of cellular disruption used, on the quantity of BFE (B-phycoerythrin) (■),allophycocyanin (▨),and R-phycocyanin (▨),obtained, respectively.

With particular reference to FIG. 2, the intracellular proteinaceous colorants BFE, AFC, and RFC which are produced by *Porphyridium cruentum* (ATCC No. 50161) are liberated by cellular disruption by a manual technique (maceration) or by ultrasound exposure. The biomass produced by the culturing of *Porphyridium cruentum* (ATCC No. 50161) is recovered by centrifugation (5 G, 5 min). Cellular disruption by manual maceration is carried out in a ceramic mortar pre-cooled in an ice bath. The wet biomass is introduced to the mortar, and for each gram of biomass used 4 cc of double distilled water and 0.98 g glass granules are added. The time of maceration is determined based on the amount of biomass being processed, namely 15 minutes per gram. Cellular disruption using ultrasound is carried out with a "Branson 1510" ultrasound unit. Into a 50 cc glass tube, 5 g wet biomass is introduced, and 20 cc distilled water is added. The mixture is stirred manually using a glass stirring rod, using circular movements, to bring the cells into suspension. The glass tube is introduced into the ultrasound unit, and the cellular suspension is subjected to ultrasound for 50 minutes. Analysis of the cellular homogenate reveals that the concentration of BFE liberated using ultrasound is 5.5 times greater than that obtained from manual maceration. From a total volume of crude extract of 25 cc (with density c. 1.2 g/cc), 5.5 mg BFE is obtained. The "purity" of the BFE obtained in the crude extract is 0.7 (Abs 545 mm/280 mm=0.7). The concentrations of BFE, AFC, and RFC are estimated using the system of equations reported by Bermejo et al. (2002).

Example 3

Figure 3:
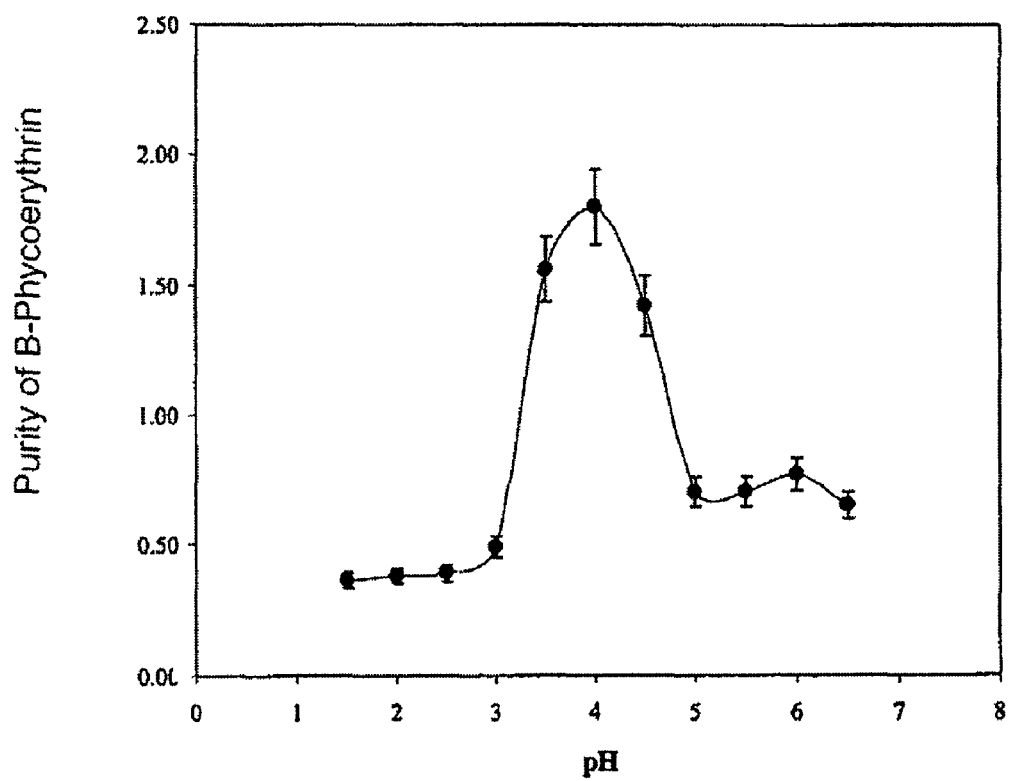
FIG. 3 shows the "purity" of the BFE as the re-suspended extract obtained from the isoelectrically precipitated precipitate, plotted versus the pH.

Isoelectric Precipitation of the BFE Extract 50 cc crude BFE extract is prepared (with concentration 0.2 mg BFE/cc) and is separated into 1.5 cc aliquots in microcentrifuge tubes. The contents of the different tubes are adjusted to different pH values (1.5, 2.0, 2.5, 3.0, 3.5, 4.0, 4.5, 5.0, 5.5, 6.0, and 6.5), as a means of determining the pH at which isoelectric precipitation occurs. The pH adjustments are made using 0.1 N HCl. Each tube is agitated using an inversion mixer (60 rpm, 2 min), then is held at rest 10 min at 10° C. to allow agglomeration of the BFE. Then the mixture is centrifuged at 200 G 10 min. Following the centrifugation, the supernatant is removed by decantation. The precipitate is re-suspended in 1.5 cc phosphate buffer (20 mM, pH 7.0). For each pH value, the concentration and "purity" of BFE in the re-suspended crude extract are estimated (Abs 545 mm/280 mm). It is found that the maximum "purity" of BFE in the re-suspended extract is obtained at pH 3.5-4.5 (see FIG. 3). The recovery of BFE in the isoelectric precipitation step is c. 78%.

Example 4

Purification of the BFE Precipitate Using Two-Aqueous-Phase Systems

To prepare a system of two aqueous phases of 50 g total weight (29 wt. % PEG (1000 g/gmol), 9 wt. % potassium phosphate, and 40 wt. % re-suspended precipitated BFE), in a plastic conical tube of capacity 50 cc there are mixed 18.1 g of 80 wt. % PEG 1000, 11.3 g of 40 wt. % potassium phosphate solution, 20.0 g re-suspended extract from the isoelectric precipitation, and 0.6 g distilled water. The contents of the tube are agitated in an inversion mixer (60 rpm, 10 min), followed by centrifugation (200 G, 10 min). The top phase of the system is recovered (total volume recovered=39 cc). The concentration of the BFE in this top phase is 0.055 mg/cc; thus the total weight of BFE in the top phase is 2.14 mg. Based on the 2.33 mg BFE introduced to the system, the recovery of the BFE from the two-aqueous-phase system is 92% of the BFE in the top phase. The "purity" of the BFE in the top phase of the system is 4.1 ("analytical grade" material, acceptable for use in molecular biology applications). The overall recovery of BFE in the process (considering losses during the isoelectric precipitation and in the two-aqueous-phase system) is c. 72%. The yields in the steps of cellular disruption, isoelectric precipitation, and two-aqueous-phase systems, along with the range of "purities" of the BFE obtained in each such step, are presented in Table 2.

TABLE 2

Yields of the steps beginning with the cellular disruption step

| Process step | Range of "purities" of BFE (Abs 545 mm/Abs 280 mm) | Yield from the step | Cumulative yield |
| --- | --- | --- | --- |
| Cellular disruption (by ultrasound) | 0.6-0.8 | 100% | 100% |
| Isoelectric precipitation (pH 4) | 1.6-2.0 | 78% | 78% |
| System of two aqueous phases | 4.0-4.2 | 92% | 72% |

We claim:

1. A method of producing B-phycoerythrin (BFE) of analytical purity, from cultures of *Porphyridium cruentum* (ATCC No. 50161); characterized in that it comprises the following steps:
   (a) culturing of *Porphyridium cruentum* (ATCC No. 50161);
   (b) separation of the biomass;
   (c) disrupting the cells of *Porphyridium cruentum* (ATCC No. 50161);
   (d) isoelectric precipitation;
   (e) recovery of the precipitate;
   (f) introducing the recovered precipitate into a two-aqueous-phase system;
   (g) recovery of the top phase of the system; and
   (h) ultrafiltration to produce BFE of analytical purity.

2. A method of producing B-phycoerythrin in analytical purity according to claim 1, characterized in that in step (a), optionally $CO_2$ may be added to the air supply flow to the bioreactor.

3. A method of producing B-phycoerythrin in analytical purity according to claim 2, characterized in that in step (a), $CO_2$ is added in a concentration of 1-5 vol %, and the duration of the culture is 15 days.

4. A method of producing B-phycoerythrin in analytical purity according to claim 2, characterized in that in step (a), no extra $CO_2$ is added, and the duration of the culture is 30 days.

5. A method of producing B-phycoerythrin in analytical purity according to claim 1, characterized in that step (b) is realized using conventional techniques such as sedimentation and/or centrifugation.

6. A method of producing B-phycoerythrin in analytical purity according to claim 5, characterized in that preferably step (b) is realized by centrifugation at 500-10,000 G, for duration 2-10 minutes.

7. A method of producing B-phycoerythrin in analytical purity according to claim 6, characterized in that step (b) is realized by centrifugation at 1000 G for 5 minutes.

8. A method of producing B-phycoerythrin in analytical purity according to claim 1, characterized in that step (c) is realized by maceration or ultrasound exposure.

9. A method of producing B-phycoerythrin in analytical purity according to claim 8, characterized in that in step (c) ultrasound exposure is used, 2-10 cc of double distilled water is added per gram of wet biomass, and the ultrasound exposure is 2-20 min per gram of wet biomass.

10. A method of producing B-phycoerythrin in analytical purity according to claim 9, characterized in that in step (c) ultrasound exposure is used, 4 cc of double distilled water is added per gram of wet biomass, and the ultrasound exposure is 10 min per gram of wet biomass.

11. A method of producing B-phycoerythrin in analytical purity according to claim 1, characterized in that in step (d) a precipitate comprising BFE is produced by isoelectric precipitation.

12. A method of producing B-phycoerythrin in analytical purity according to claim 1, characterized in that in step (d) the pH is adjusted to between 4 and 5 with acid or base at a temperature in the range 5-15° C., and the mixture is protected from light.

13. A method of producing B-phycoerythrin in analytical purity according to claim 12, characterized in that in step (d) the acid employed may be chosen from the following: hydrochloric acid (HCl), sulfuric acid ($H_2SO_4$), phosphoric acid ($H_3PO_4$), and acetic acid ($CH_3COOH$), at a concentration of 0.1-10 N.

14. A method of producing B-phycoerythrin in analytical purity according to claim 13, characterized in that in step (d) the acid employed is preferably HCl at a concentration of 0.1-10 N, preferably 1.0 N.

15. A method of producing B-phycoerythrin in analytical purity according to claim 12, characterized in that in step (d) the base employed may be chosen from the following: sodium hydroxide (NaOH), at a concentration of 0.1-10 N.

16. A method of producing B-phycoerythrin in analytical purity according to claim 12, characterized in that in step (d) the pH is preferably adjusted to 4.

17. A method of producing B-phycoerythrin in analytical purity according to claim 12, characterized in that in step (d) the temperature is preferably 10° C.

18. A method of producing B-phycoerythrin in analytical purity according to claim 12, characterized in that in step (d) the total light exposure is no greater than 20 microeinstein, for less than 30 min.

19. A method of producing B-phycoerythrin in analytical purity according to claim 1, characterized in that step (e) is realized by centrifugation (100-2000 G, 10-20 min), with a phosphate buffer.

20. A method of producing B-phycoerythrin in analytical purity according to claim 19, characterized in that step (e) is realized by centrifugation, preferably at 1000 G, for 10 min, with a phosphate buffer at concentration 20 mM and pH 7.

21. A method of producing B-phycoerythrin in analytical purity according to claim 1, characterized in that step (f) consists of application of two-aqueous-phase systems comprised of PEG and potassium phosphate, with the following parameters:
   molecular weight of the polymer (MW PEG) in the range 600-1500 g/gmol;
   length of the "cut line" (LLC) (which is a function of the difference between the concentration of the PEG and the concentration of the salt in each of the phases in the system) in the range 30-50 wt. %;
   volume ratio ($V_R$) (defined as the ratio between volume of the upper phase and the volume of the lower phase, in the system) greater than 2; and
   pH of the system between 7 and 8.

22. A method of producing B-phycoerythrin in analytical purity according to claim 1, characterized in that step (g) is realized using membranes with pore size 10-100 kilodaltons (kDa).

23. A method of producing B-phycoerythrin in analytical purity according to claim 22, characterized in that in step (g), preferably membranes are used which have pore size 50 kilodaltons (kDa).

24. A method of producing B-phycoerythrin in analytical purity for applications in molecular biology, characterized in that the B-phycoerythrin has analytical "purity" as defined greater than 4.

* * * * *